(12) United States Patent
Souter

(10) Patent No.: US 8,008,241 B2
(45) Date of Patent: Aug. 30, 2011

(54) AUTOMATIC DISHWASHING DETERGENT COMPOSITION

(75) Inventor: Philip Frank Souter, Morpeth (GB)

(73) Assignee: The Procter & Gamble Company, Cincinnati, OH (US)

( * ) Notice: Subject to any disclaimer, the term of this patent is extended or adjusted under 35 U.S.C. 154(b) by 135 days.

(21) Appl. No.: 12/397,489

(22) Filed: Mar. 4, 2009

(65) Prior Publication Data

US 2009/0233831 A1 Sep. 17, 2009

(30) Foreign Application Priority Data

Mar. 14, 2008 (EP) .................................... 08152749
Sep. 18, 2008 (EP) .................................... 08164650

(51) Int. Cl.
*C11D 3/386* (2006.01)
*C12N 9/54* (2006.01)
*C12N 9/28* (2006.01)

(52) U.S. Cl. ................. 510/226; 435/202; 435/221
(58) Field of Classification Search ............. 510/226; 435/221
See application file for complete search history.

(56) References Cited

U.S. PATENT DOCUMENTS

| | | | |
|---|---|---|---|
| 4,227,084 A | 10/1980 | Thomann et al. | |
| 4,246,612 A | 1/1981 | Berry et al. | |
| 4,760,025 A | 7/1988 | Estell et al. | |
| 4,765,916 A | 8/1988 | Ogar et al. | |
| 4,810,410 A | 3/1989 | Diakun et al. | |
| 4,972,017 A | 11/1990 | Smith et al. | |
| 5,114,611 A | 5/1992 | Van Kralingen et al. | |
| 5,679,630 A | 10/1997 | Baeck et al. | |
| 5,856,164 A | 1/1999 | Outtrup et al. | |
| 6,287,841 B1 * | 9/2001 | Mulleners et al. | 435/221 |
| 6,312,936 B1 | 11/2001 | Poulose et al. | |
| 6,380,147 B1 | 4/2002 | Speckmann et al. | |
| 6,426,229 B1 | 7/2002 | Yamamoto et al. | |
| 6,939,702 B1 | 9/2005 | Vind et al. | |

FOREIGN PATENT DOCUMENTS

| | | |
|---|---|---|
| DE | 102005062984 A1 | 7/2007 |
| WO | WO 9102792 A1 | 3/1991 |
| WO | WO 9402618 A1 | 2/1994 |
| WO | WO 9510591 * | 4/1995 |
| WO | WO 0242408 A2 | 5/2002 |
| WO | WO 2008/010925 A2 | 1/2008 |

OTHER PUBLICATIONS

"Stainzyme: a breakthrough in dishwashing performance" Focus on Surfactants, Elsevier, vol. 2004, No. 12, Dec. 1, 2004, p. 3, XP004699512 ISSN: 1351-4210.

* cited by examiner

*Primary Examiner* — Tekchand Saidha
(74) *Attorney, Agent, or Firm* — Melissa G Krasovec; Leonard W Lewis

(57) ABSTRACT

An automatic dishwashing detergent composition comprising:
a. at least 0.1 mg of active protease per gram of composition, wherein the protease is a variant of a protease that has at least 70% identity with the amino acid sequence of SEQ ID NO:1. wherein said variant comprise variations in one or more of the following positions: 32, 33, 48-54, 58-62, 94-107, 116, 123-133, 150, 152-156, 158-161, 164, 169, 175-186, 197, 198, 203-216 as compared with the protease in SEQ ID NO:1; and
b. at least 0.05 mg of an active low temperature amylase per gram of composition.

10 Claims, No Drawings

AUTOMATIC DISHWASHING DETERGENT COMPOSITION

TECHNICAL FIELD

The present invention is in the field of detergents. In particular, it relates to an automatic dishwashing detergent composition comprising a new enzymatic system. The composition provides excellent cleaning and finishing, it is environmentally friendlier than traditional compositions and allows for a more energy efficient automatic dishwashing process.

BACKGROUND

Automatic dishwashing detergents have improved over time but still some of the consumer needs are unmet in terms of both cleaning and finishing. In recent years there has been an ever increasing trend towards safer and environmentally friendly detergent compositions. This trend imposes additional constrains onto the automatic dishwashing formulator. In terms of energy efficiency and raw material savings, it is desirable to design products which provide good performance even at low temperatures and with a reduction on the amount of chemicals, in particular non-readily biodegradable chemicals.

A frequent problem found in automatic dishwashing is the presence of grit on washed items. Grit is sometimes found in dishware/tableware after the automatic dishwashing process even if the items were free of it before they went into the dishwasher. It seems that grit is formed during the dishwashing process. The mechanism of grit formation is not well understood. It maybe due to the high temperatures and combination of different soils lifted from the soiled items during the dishwashing process. Somehow, the different soils seem to recombine to give rise to grit which deposits onto the surface of the washed items. Once the grit is formed and deposited it is very difficult to remove it. The problem seems to be more acute when detergents in unit dose form are used.

Another frequently found and unsolved problem is the presence of filming and spotting on washed items, this is particularly noticeable in glass and metal items.

In view of the above discussion, an objective of the present invention is to provide a more eco-friendly product that at the same time provides excellent cleaning and finishing benefits.

SUMMARY OF THE INVENTION

According to a first aspect of the present invention, there is provided an automatic dishwashing detergent composition comprising an improved enzymatic system comprising an improved protease (a variant protease as described herein below) in combination with a low temperature amylase (as described herein below). The composition of the invention provides cleaning and finishing benefits across a wide range of temperatures, including low temperatures, improving the energy profile of the dishwashing process. Surprisingly, the composition of the invention allows for a more energy efficient dishwashing processes without compromising in cleaning and finishing.

The variant protease for use in the composition of the invention is a protease wherein the variations are made versus a protease that has at least 70%, preferably at least 90%, more preferably at least 95%, even more preferably at least 99% and especially 100% identity with the amino acid sequence of SEQ ID NO:1. Said variant protease comprises substitutions in one or more of the following positions: 32, 33, 48-54, 58-62, 94-107, 116, 123-133, 150, 152-156, 158-161, 164, 169, 175-186, 197, 198, 203-216 as compared with the protease in SEQ ID NO:1. Excellent results in terms of cleaning and finishing (including absence of spotting and filming and excellent shine) have been obtained when the variant protease comprises the following variations: G116V+S126L+P127Q+S128A.

Particularly good results are obtained when the variant protease is used in combination with a low temperature amylase which is either:

(a) a variant comprising one or more, preferably three or more substitutions in the following positions versus SEQ ID NO: 2:
9, 26, 149, 182, 186, 202, 257, 295, 299, 323, 339 and 345; and (b) optionally with one or more, preferably all of the substitutions and/or deletions in the following positions: 118, 183, 184, 195, 320 and 458, which if present preferably comprise R118K, D183*, G184*, N195F, R320K and/or R458K.

or:

(c) a variant comprising at least one substitution in the following positions versus SEQ ID NO:4: M202, M208, S255, R172, and/or M261. Preferably said amylase comprises one or more of M202L, M202V, M202S, M202T, M202I, M202Q, M202W, S255N and/or R172Q. Particularly preferred are those comprising the M202L or M202T mutations.

Preferred low temperature amylases include those comprising the following sets of mutations:

(i) M9L+, M323T;
(ii) M9L+M202L/T/V/I+M323T;
(iii) M9L+N195F+M202L/V/I+M323T;
(iv) M9L+R118K+D183*+G184*+R320K+M323T+R458K;
(v) M9L+R118K+D183*+G184*+M202L/T/V/I; R320K+M323T+R458K;
(vi) M9L+G149A+G182T+G186A+M202L+T257I+Y295F+N299Y+M323T+A339S+E345R;
(vii) M9L+G149A+G182T+G186A+M202I+T257I+Y295F+N299Y+M323T+A339S+E345R;
(viii) M9L+R118K+G149A+G182T+D183*+G184*+G186A+M202L+T257I+Y295F+N299Y+R320K+M323T+A339S+E345R+R458K;
(ix) M9L+R118K+G149A+G182T+D183*+G184*+G186A+N195F+M202L+T257I+Y295F+N299Y+R320K+M323T+A339S+E345R+R458K; (x) M9L+R118K+G149A+G182T+D183*+G184*+G186A+M202I+T257I+Y295F+N299Y+R320K+M323T+A339S+E345R+R458K;
(xi) M9L+R118K+D183*+D184*+N195F+M202L+R320K+M323T+R458K;
(xii) M9L+R118K+D183*+D184*+N195F+M202T+R320K+M323T+R458K;
(xiii) M9L+R118K+D183*+D184*+N195F+M202I+R320K+M323T+R458K;
(xiv) M9L+R118K+D183*+D184*+N195F+M202V+R320K+M323T+R458K;
(xv) M9L+R118K+N150H+D183*+D184*+N195F+M202L+V214T+R320K+M323T+R458K; or
(xvi) M9L+R118K+D183*+D184*+N195F+M202L+V214T+R320K+M323T+E345N+R458K.

The most preferred amylase is the variant sold under the tradename Stainzyme Plus™ (Novozymes A/S, Bagsvaerd, Denmark).

A further preferred set of low temperature amylases are those derived from *Bacillus* sp. 707, whose sequence is shown as SEQ ID NO: 4, preferably comprising one or more of the following mutations M202, M208, S255, R172, and/or M261. Preferably said amylase comprises one or more of M202L, M202V, M202S, M202T, M202I, M202Q, M202W, S255N and/or R172Q. Particularly preferred are those variants comprising the M202L or M202T mutations.

In preferred embodiments, the composition comprises a high level of amylase, at least 0.2 mg of active amylase per gram of composition, preferably from about 0.2 to about 10, more preferably from about 0.25 to about 6, specially preferred from about 0.3 to about 4 mg of active amylase per gram of composition. It has been found that compositions comprising a high level of amylase help to prevent grit formation during the automatic dishwashing process and provide good cleaning and finishing results. Better results in terms of grit removal can be achieved when the composition comprises a lipase, thus in a preferred embodiment the composition of the invention comprise a lipase, preferably a lipase derived from the *Humicola Lanuginosa* wild -type that contains the mutations T231R and N233R. Compositions comprising Lipex® (Novozymes A/S, Bagsvaerd, Denmark) have been found particularly effective in terms of grit prevention.

The cleaning results can be further improved by adding a high level of protease to the composition. Thus, in further preferred embodiments, the composition comprises a high level of protease, in particular at least 1.5 mg of active protease per gram of composition. Preferred levels of protease in the compositions of the invention include from about 1.5 to about 10, more preferably from about 1.8 to about 5 and especially from about 2 to about 4 mg of active protease per grams of composition. The biodegradability of the compositions of the invention is further improved when a high level of enzyme is present. The high level of enzyme allows for a reduction on the level of non-biodegradable ingredients of the product and at the same time improves cleaning and finishing performance.

In especially preferred embodiments, the composition comprises an anti-redeposition agent and/or sulfonated polymer. Excellent finishing results are obtained with compositions comprising an anti-redeposition agent or a sulfonated polymer and in particular compositions comprising a combination thereof. Benefits are seen in terms of reduction/prevention of filming, spotting and improvement on shine. Shine on washed items seem to be an unsolved problem, in particular in stressed cases of highly soiled loads. The compositions of the invention provide shine benefits even under stressed conditions. These benefits, under stressed conditions, are not easily achievable with compositions lacking the enzymatic system of the invention.

In preferred embodiments, the compositions of the invention reduce the particle size of the soil fragments and/or molecular weight as compared to that obtained with traditional detergent compositions. This facilitates the suspension of the soils in the wash liquor. Soil suspension can further be improved by an anti-redeposition agent. The anti-redeposition agent contributes to keep detached soils as individual entities in solution and prevents re-combination that can give rise to grit formation. These agents can also help to detach soils from the soiled surfaces. This in combination with soil suspension contributes to a more effective enzymatic cleaning and results in better shine and reduced filming and spotting on the washed items. Preferred anti-redeposition agents are non-ionic surfactants, in particular non-ionic surfactants having a phase inversion temperature (PIT) in the range of from about 40 to about 70° C. Compositions comprising non-ionic surfactants having a PIT in this temperature range provide very good cleaning. The anti-redeposition agent may also help the enzymes to get to the soiled substrates. The anti-redeposition agent seems to help with the cleaning during the main wash. Some of the anti-redeposition agent is carried over to the rinse cycle where it helps with sheeting thereby reducing/eliminating filming and spotting. Surfactants, having a PIT in the claimed range, present cleaning properties during the main wash and sheeting properties during the rinse. In other preferred embodiments the anti-redeposition agent is a non-ionic surfactant having a Draves wetting time (as measured using the standard method ISO 8022 under the following conditions; 3-g hook, 5-g cotton skein, 0.1% by weight aqueous solution at a temperature of 25° C.) of less than about 360 seconds, preferably less than 60 seconds.

It is also preferred that the compositions of the invention comprise a metal care agent, in particular a zinc salt.

In preferred embodiments the composition of the invention is in unit dose form. Products in unit dose form include tablets, capsules, sachets, pouches, etc. Preferred for use herein are tablets wrapped with a water-soluble film and water-soluble pouches. The weight of the composition of the invention is from about 10 to about 25 grams, preferably from about 12 to about 24 grams and more preferably from 14 to 22 grams. These weights are extremely convenient for automatic dishwashing product dispenser fit. In the cases of unit dose products having a water-soluble material enveloping the detergent composition, the water-soluble material is not considered as part of the composition.

In preferred embodiments the unit dose form is a water-soluble pouch (i.e., water-soluble film enveloping a detergent composition), preferably a multi-compartment pouch having a plurality of films forming a plurality of compartments. This configuration contributes to the flexibility and optimization of the composition. It allows for the separation and controlled release of different ingredients. Preferably one compartment contains a composition in solid form and another compartment contains a composition in liquid form.

In preferred multi-compartment pouch embodiments two different compartments contain anti-redeposition agent. Preferably the films of these two compartments have different dissolution profiles, allowing the release of the same or different anti-redeposition agents at different times. For example, anti-redeposition agent from one compartment (first compartment) can be delivered early in the washing process to help with soil removal and anti-redeposition agent from another compartment (second compartment) can be delivered at least two minutes, preferably at least five minutes later than the anti-redeposition agent from the first compartment. Ideally, the enzymes should be delivered after the anti-redeposition agent from the first compartment and before the anti-redeposition agent from the second compartment.

Especially preferred for use herein is a multi-compartment pouch comprising two side-by-side compartments superposed onto another compartment wherein at least two different compartments contain two different compositions.

According to the second aspect of the invention, there is provided a method of dishwashing in an automatic dishwashing machine using the detergent composition of the invention and comprising the steps of placing the composition into the product dispenser and releasing it during the main-wash cycle.

In preferred process embodiments, anti-redeposition agents are delivered at two different times of the dishwashing process.

According to the third aspect of the invention, there is provided the use of the detergent composition of the invention for automatic dishwashing at low temperature (i.e., the main-wash temperature is no more than 50, preferably no more than 45 and more preferably no more than 40° C.).

DETAILED DESCRIPTION OF THE INVENTION

The present invention envisages an automatic dishwashing detergent composition comprising a new enzymatic system. The system comprises an improved protease and a low temperature amylase and optionally a lipase. The compositions of the invention prevent grit formation on washed items, which is one of the problems currently found in automatic dishwashing. The composition provides excellent cleaning and finishing results and it is environmentally friendly in terms of energy and raw material reduction. The present invention also envisages a method of dishwashing using the composition of the invention.

Enzyme Related Terminology
  Nomenclature for Amino Acid Modifications
  In describing enzyme variants herein, the following nomenclature is used for ease of reference: Original amino acid(s):position(s):substituted amino acid(s).
  According to this nomenclature, for instance the substitution of glutamic acid for glycine in position 195 is shown as G195E. A deletion of glycine in the same position is shown as G195*, and insertion of an additional amino acid residue such as lysine is shown as G195GK. Where a specific enzyme contains a "deletion" in comparison with other enzyme and an insertion is made in such a position this is indicated as *36D for insertion of an aspartic acid in position 36. Multiple mutations are separated by pluses, i.e.: S99G+V102N, representing mutations in positions 99 and 102 substituting serine and valine for glycine and asparagine, respectively. Where the amino acid in a position (e.g. 102) may be substituted by another amino acid selected from a group of amino acids, e.g. the group consisting of N and I, this will be indicated by V102N/I.
  In all cases, the accepted IUPAC single letter or triple letter amino acid abbreviation is employed.
  Protease Amino Acid Numbering
  The numbering used in this patent is numbering versus the specific protease (PB92) listed as SEQ ID No: 1. An alternative numbering scheme is the so-called BPN' numbering scheme which is commonly used in the art. For convenience the numbering schemes are compared below in Table 1:

TABLE 1

| Protease Mutation numbering | |
|---|---|
| PB92 numbering of this patent (numbering versus SEQ ID NO: 1) | Equivalent BPN' numbering |
| G116V + S126L + P127Q + S128A | G118V + S128L + P129Q + S130A |
| G116V + S126N + P127S + S128A + S160D | G118V + S128N + P129S + S130A + S166D |
| G116V + S126L + P127Q + S128A + S160D | G118V + S128L + P129Q + S130A + S166D |
| G116V + S126V + P127E + S128K | G118V + S128V + P129E + S130K |
| G116V + S126V + P127M + S160D | G118V + S128V + P129M + S166D |
| S128T | S130T |
| G116V + S126F + P127L + S128T | G118V + S128F + P129L + S130T |
| G116V + S126L + P127N + S128V | G118V + S128L + P129N + S130V |
| G116V + S126F + P127Q | G118V + S128F + P129Q |
| G116V + S126V + P127E + S128K + S160D | G118V + S128V + P129E + S130K + S166D |
| G116V + S126R + P127S + S128P | G118V + S128R + P129S + S130P |
| S126R + P127Q + S128D | S126R + P129Q + S130D |

TABLE 1-continued

| Protease Mutation numbering | |
|---|---|
| PB92 numbering of this patent (numbering versus SEQ ID NO: 1) | Equivalent BPN' numbering |
| S126C + P127R + S128D | S128LC + P129R + S130D |
| S126C + P127R + S128G | S128LC + P129R + S130G |

Amino Acid Identity
  The relatedness between two amino acid sequences is described by the parameter "identity". For purposes of the present invention, the alignment of two amino acid sequences is determined by using the Needle program from the EMBOSS package (http://emboss.org) version 2.8.0. The Needle program implements the global alignment algorithm described in Needleman, S. B. and Wunsch, C. D. (1970) J. Mol. Biol. 48, 443-453. The substitution matrix used is BLOSUM62, gap opening penalty is 10, and gap extension penalty is 0.5.
  The degree of identity between an amino acid sequence of and enzyme used herein ("invention sequence") and a different amino acid sequence ("foreign sequence") is calculated as the number of exact matches in an alignment of the two sequences, divided by the length of the "invention sequence" or the length of the "foreign sequence", whichever is the shortest. The result is expressed in percent identity. An exact match occurs when the "invention sequence" and the "foreign sequence" have identical amino acid residues in the same positions of the overlap. The length of a sequence is the number of amino acid residues in the sequence.
  Variant Protease
  The variant protease for use herein is a protease with variations versus a protease that has at least 70%, preferably at least 90%, more preferably at least 95%, even more preferably at least 99% and especially 100% identity with the amino acid sequence of SEQ ID NO:1. Said variant protease comprises substitutions in one or more of the following positions: 32, 33, 48-54, 58-62, 94-107, 116, 123-133, 150, 152-156, 158-161, 164, 169, 175-186, 197, 198, 203-216 as compared with the protease in SEQ ID NO:1. Preferably, said protease has substitutions in one or more of the following positions: 60, 94, 97-102, 105, 116, 123-128, 150, 152, 160, 183, 203, 211, 212, 213, 214 and 216. More preferably, the protease comprises mutations in one or more, even more preferably in three or more of the following positions, 116, 126, 127, 128 and 160.
  Especially preferred are variants with mutations in each of positions 116, 126, 127 and 128.
  Particularly suitable for use in the composition of the invention has been found to be a protease comprising the following specific mutations versus the enzyme of SEQ ID NO:1:
    (i) G116V+S126L+P127Q+S128A
    (ii) G116V+S126N+P127S+S128A+S160D
    (iii) G116V+S126L+P127Q+S128A+S160D
    (iv) G116V+S126V+P127E+S128K
    (v) G116V+S126V+P127M+S160D
    (vi) S128T
    (vii) G116V+S126F+P127L+S128T
    (viii) G116V+S126L+P127N+S128V
    (ix) G116V+S126F+P127Q
    (x) G116V+S126V+P127E+S128K+S160D
    (xi) G116V+S126R+P127S+S128P
    (xii) S126R+P127Q+S128D
    (xiii) S126C+P127R+S128D; or
    (xiv) S126C+P127R+S128G Especially preferred for use in the composition of the invention has been found to be a protease comprising the mutations G116V+S126L+P127Q and S128A.

Assay for Protease Activity

Protease activity is measured using Dimethyl Casein (DMC). Release of peptides is initiated via protease action. Protease activity is measured in PU's. 1 PU (protease unit) is the amount of enzyme which hydrolyzes casein such that the initial rate of formation of peptides per minute corresponds to 1 μmole of glycine per minute. 1 KPU is equal to 1000 protease units.

Analysis

A 2,4,6 Trinitrobenzenesulphonic acid (TNBSA) solution and a DMC solution are prepared. All ingredients are from Sigma-Aldrich, Milwaukee, USA, unless otherwise stated. The TNBSA solution is made by dissolving 0.40 mL of TNBSA (Sigma Cat No P-2297) in 50 mL of deionized water. The DMC solution is made by dissolving 5.09 g of Potassium Chloride (Sigma Catalogue No: P-3911) and 1.545 g of Boric Acid (Sigma Catalogue No: B-0399) in 500 mL of deionized water. The solution is stirred for 10 mins to dissolve and then the pH adjusted to 9.0 using 50% NaOH. 2 g of DMC are then added (DMC, British Drug House, Cat No. 79457) and the solution is stirred to dissolve.

100 μL of a dilute enzyme containing sample is added (0.5% sodium sulfite solution with 0.04% calcium chloride; Sigma Catalogue No: S-6672 and Sigma Catalogue No: C-5080, respectively) to 1800 μL of DMC solution. The resultant solution is mixed and incubated at 37° C. for 4 minutes. Then 900 μL of TNBSA solution are added to the mixture and incubated for another 5 minutes. The absorbance is read at 415 nm.

Preferably, the variant protease of the invention has an activity of at least 0.3 KNPU per gram of composition, more preferably at least 0.7 KNPU per gram of composition and especially 1 KNPU per gram of composition.

Additional Proteases

In the composition of the invention a mixture of two or more proteases may be used. A mixture of proteases can contribute to an enhanced cleaning across a broader temperature and/or substrate range and provide superior shine benefits, especially when used in conjunction with an anti-redeposition agent and/or a sulfonated polymer.

Suitable proteases for use in combination with the variant protease of the invention include metalloproteases and serine proteases, including neutral or alkaline microbial serine proteases, such as subtilisins (EC 3.4.21.62). Suitable proteases include those of animal, vegetable or microbial origin. Microbial origin is preferred. Chemically or genetically modified mutants are included. The protease may be a serine protease, preferably an alkaline microbial protease or a chymotrypsin or trypsin-like protease. Examples of neutral or alkaline proteases include:

(a) subtilisins (EC 3.4.21.62), especially those derived from *Bacillus*, such as *Bacillus lentus, B. alkalophilus, B. subtilis, B. amyloliquefaciens, Bacillus pumilus* and *Bacillus gibsonii* described in U.S. Pat. Nos. 6,312,936 B1, 5,679,630, 4,760,025, DE102006022216A1 and DE102006022224A1.

(b) trypsin-like or chymotrypsin-like proteases, such as trypsin (e.g., of porcine or bovine origin), the Fusarium protease described in WO 89/06270 and the chymotrypsin proteases derived from Cellumonas described in WO 05/052161 and WO 05/052146.

(c) metalloproteases, especially those derived from *Bacillus amyloliquefaciens* decribed in WO 07/044993A2.

Preferred commercially available protease enzymes include those sold under the trade names Alcalase®, Savinase®, Primase®, Durazym®, Polarzyme®, Kannase®, Liquanase®, Ovozyme®, Neutrase®, Everlase® and Esperase® by Novozymes A/S (Denmark), those sold under the tradename Maxatase®, Maxacal®, Maxapem®, Properase®, Purafect®, Purafect Prime®, Purafect Ox®, FN3®, FN4® and Purafect OXP® by Genencor International, and those sold under the tradename Opticlean® and Optimase® by Solvay Enzymes.

Especially preferred for use herein in combination with the variant protease of the invention are commercial proteases selected from the group consisting of Properase®, Purafect®, Ovozyme®, Everlase®, Savinase® and FN3®.

Low Temperature Amylases

Preferred amylases for use herein are low temperature amylases. Compositions comprising low temperature amylases allow for a more energy efficient dishwashing processes without compromising in cleaning.

As used herein, "low temperature amylase" is an amylase that demonstrates at least 1.2, preferably at least 1.5 and more preferably at least 2 times the relative activity of the reference amylase at 25° C. As used herein, the "reference amylase" is the amylase of SEQ ID NO:3, commercially available under the tradename of Termamyl™ (Novozymes A/S). As used herein, "relative activity" is the fraction derived from dividing the activity of the enzyme at the temperature assayed versus its activity at its optimal temperature measured at a pH of 9.

Preferably low temperature amylases possess one or more of the following properties:

(a) greater than or equal to 60%, preferably 70%, more preferably 80% and especially 90% of their maximum activity at 50° C.

(b) greater than or equal to 30%, preferably 40%, more preferably 50%, even more preferably 60% and especially 70% of their maximum activity at 40° C.

(c) greater than or equal to 20%, preferably 30% more preferably 40% of their maximum activity at 30° C.

Activity may be determined by well-known standard amylase assays described herein below and is assayed between 20 and 90° C.

Low temperature amylases for use herein, including chemically or genetically modified mutants (variants), are alkaline amylases possessing at least 90%, preferably 95%, more preferably 98%, even more preferably 99% and especially 100% identity, with those derived from *Bacillus* sp. NCIB 12289, NCIB 12512, NCIB 12513, DSM 9375 (U.S. Pat. No. 7,153,818) DSM 12368, DSMZ no. 12649, KSM AP1378 (WO 97/00324), *Bacillus* sp. 707, KSM K36 or KSM K38 (EP 1,022,334). Preferred low temperature amylases include:

(a) the variants described in U.S. Pat. No. 5,856,164 and WO99/23211, WO 96/23873, WO00/60060 and WO 06/002643, especially the variants with one or more substitutions in the following positions versus SEQ ID No: 2: 9, 26, 30, 33, 82, 37, 106, 118, 128, 133, 149, 150, 160, 178, 182, 186, 193, 195, 202, 203, 214, 231, 256, 257, 258, 269, 270, 272, 283, 295, 296, 298, 299, 303, 304, 305, 311, 314, 315, 318, 319, 320, 323, 339, 345, 361, 378, 383, 419, 421, 437, 441, 444, 445, 446, 447, 450, 458, 461, 471, 482, 484 that also preferably contain the deletions of D183* and G184*.

(b) variants exhibiting at least 90% identity with the wild-type enzyme from *Bacillus* SP722 (SEQ ID No. 4 in WO06/002643, p. 7-9 of sequence listings), especially variants with deletions in the 183 and 184 positions and variants described in WO 00/60060, which is incorporated herein by reference.
  (c) variants exhibiting at least 95% identity with SEQ ID NO:4, the wild-type enzyme from Bacillus sp. 707, especially those comprising mutations in one or more of the following positions M202, M208, S255, R172, and/or M261.

Preferred commercially available low temperature amylases for use herein are STAINZYME®, STAINZYME PLUS®, STAINZYME ULTRA® and NATALASE® (Novozymes A/S).

In a preferred embodiment the low temperature amylase is a variant with either:
  (a) one or more, preferably three or more substitutions in the following positions versus SEQ ID NO: 2:
    9, 26, 149, 182, 186, 202, 257, 295, 299, 323, 339 and 345; and
  (b) optionally with one or more, preferably all of the substitutions and/or deletions in the following positions: 118, 183, 184, 195, 320 and 458, which if present preferably comprise R118K, D183*, G184*, N195F, R320K and/or R458K.
or:
  (c) at least one substitution in the following positions versus SEQ ID NO:4: M202, M208, S255, R172, and/or M261. Preferably said amylase comprises one or more of M202L, M202V, M202S, M202T, M202I, M202Q, M202W, S255N and/or R172Q. Particularly preferred are those comprising the M202L or M202T mutations.

Preferred low temperature amylases include those comprising the following sets of mutations:
  (i) M9L+M323T;
  (ii) M9L+M202L/T/V/I+M323T;
  (iii) M9L+N195F+M202L/T/V/I+M323T;
  (iv) M9L+R118K+D183*+G184*+R320K+M323T+R458K;
  (v) M9L+R118K+D183*+G184*+M202L/T/V/I+R320K+M323T+R458K;
  (vi) M9L+G149A+G182T+G186A+M202L+T257I+Y295F+N299Y+M323T+A339S+E345R;
  (vii) M9L+G149A+G182T+G186A+M202I+T257I+Y295F+N299Y+M323T+A339S+E345R;
  (viii) M9L+R118K+G149A+G182T+D183*+G184*+G186A+M202L+T257I+Y295F+N299Y+R320K+M323T+A339S+E345R+R458K;
  (ix) M9L+R118K+G149A+G182T+D183*+G184*+G186A+N195F+M202L+T257I+Y295F+N299Y+R320K+M323T+A339S+E345R+R458K;
  (x) M9L+R118K+G149A+G182T+D183*+G184*+G186A+M202I+T257I+Y295F+N299Y+R320K+M323T+A339S+E345R+R458K;
  (xi) M9L+R118K+D183*+D184*+N195F+M202L+R320K+M323T+R458K;
  (xii) M9L+R118K+D183*+D184*+N195F+M202T+R320K+M323T+R458K;
  (xiii) M9L+R118K+D183*+D184*+N195F+M202I+R320K+M323T+R458K;
  (xiv) M9L+R118K+D183*+D184*+N195F+M202V+R320K+M323T+R458K;
  (xv) M9L+R118K+N150H+D183*+D184*+N195F+M202L+V214T+R320K+M323T+R458K; or
  (xvi) M9L+R118K+D183*+D184*+N195F+M202L+V214T+R320K+M323T+E345N+R458K.

The most preferred amylase is the variant sold under the tradename Stainzyme Plus™ (Novozymes A/S, Bagsvaerd, Denmark).

Preferred for use herein is a combination of a mixture of two or more low temperature amylases. A mixture of amylases can contribute to an enhanced cleaning across a broader temperature and/or substrate range and provide superior shine benefits, especially when used in conjunction with an anti-redeposition agent and/or a sulfonated polymer.

Assay for Alpha-Amylase Activity

Amylase activity is measured using a maltoheptaoside modified with a p-Nitrophenol chromophore (Infinity Amylase Reagent from Thermo Electron, Woburn, Mass., USA, Cat #: TR25421). Release of the chromophore is initiated via amylase action. Amylase activity is measured initially in AMU's. 1 AMU (amylase unit) is the amount of enzyme which hydrolyzes PNP-G7 (p-nitrophenyl-alpha,D-maltoheptaoside) carbohydrate substrate such that the initial rate of formation of small carbohydrates (G2-4) per minute corresponds to 1 μmole of 4-Nitrophenol per minute.

The test is run versus a reference enzyme, that of SEQ ID No:3 sold under the tradename Termamyl™ (Novozymes A/S). These amylase units (AMUs) are converted into a unit of kNU, using the conversion factor 0.133 mg of Termamyl™ corresponds to 1 KNU. Therefore if using the above assay the enzyme sample shows an activity equivalent to that shown by 0.266 mg of Termamyl™, its activity is considered to be 2 KNU.

Analysis

200 μL of dilute enzyme containing sample is added to 2500 μL of Infinity amylase reagent. Mix and incubate at 37° C. for 4.5 minutes. The absorbance is read at 415 nm.

Preferably, the low temperature amylase in the composition of the invention has an activity of at least 6 KNU, more preferably at least 7.5 KNU per gram of detergent composition.

Additional Enzymes

Additional enzymes suitable for use in the composition of the invention can comprise one or more enzymes selected from the group comprising hemicellulases, cellulases, cellobiose dehydrogenases, peroxidases, proteases, xylanases, lipases, phospholipases, esterases, cutinases, pectinases, mannanases, pectate lyases, keratinases, reductases, oxidases, phenoloxidases, lipoxygenases, ligninases, pullulanases, tannases, pentosanases, malanases, β-glucanases, arabinosidases, hyaluronidase, chondroitinase, laccase, amylases, and mixtures thereof.

In preferred embodiments, such additional enzyme may be selected from the group consisting of lipases, including "first cycle lipases" comprising a substitution of an electrically neutral or negatively charged amino acid with R or K at any of positions 3, 224, 229, 231 and 233 on the wild-type of Humicola Lanuginosa, whose sequence is shown as SEQ ID No 1 in pages 5 and 6 of U.S. Pat. No. 6,939,702 B1, preferably a variant comprising T231R and N233R mutations. One such preferred variant is sold under the tradename Lipex® (Novozymes A/S, Bagsvaerd, Denmark).

Enzyme stabilizer components—Suitable enzyme stabilizers include oligosaccharides, polysaccharides and inorganic divalent metal salts, such as alkaline earth metal salts, especially calcium salts. Chlorides and sulphates are preferred with calcium chloride an especially preferred calcium salt according to the invention. Examples of suitable oligosaccharides and polysaccharides, such as dextrins, can be found in WO07/145964A2 which is incorporated herein by reference. In case of aqueous compositions comprising protease, a reversible protease inhibitor, such as a boron compound, inckuding borate and 4-formyl phenyl boronic acid or a tripeptide aldehyde, can be added to further improve stability.

Anti-redeposition Agent

Suitable for use herein as anti-redeposition agents are non-ionic surfactants. Traditionally, non-ionic surfactants have been used in automatic dishwashing for surface modification purposes in particular for sheeting to avoid filming and spotting and to improve shine. It has been found that in the compositions of the invention non-ionic surfactants contribute to prevent redeposition of soils.

In preferred embodiments the anti-redeposition agent is a non-ionic surfactant or a non-ionic surfactant system having a phase inversion temperature, as measured at a concentration of 1% in distilled water, between 40 and 70° C., preferably between 45 and 65° C. By a "non-ionic surfactant system" is meant herein a mixture of two or more non-ionic surfactants. Preferred for use herein are non-ionic surfactant systems. They seem to have improved cleaning and finishing properties and better stability in product than single non-ionic surfactants.

Phase inversion temperature is the temperature below which a surfactant, or a mixture thereof, partitions preferentially into the water phase as oil-swollen micelles and above which it partitions preferentially into the oil phase as water swollen inverted micelles. Phase inversion temperature can be determined visually by identifying at which temperature cloudiness occurs.

The phase inversion temperature of a non-ionic surfactant or system can be determined as follows: a solution containing 1% of the corresponding surfactant or mixture by weight of the solution in distilled water is prepared. The solution is stirred gently before phase inversion temperature analysis to ensure that the process occurs in chemical equilibrium. The phase inversion temperature is taken in a thermostable bath by immersing the solutions in 75 mm sealed glass test tube. To ensure the absence of leakage, the test tube is weighed before and after phase inversion temperature measurement. The temperature is gradually increased at a rate of less than 1° C. per minute, until the temperature reaches a few degrees below the pre-estimated phase inversion temperature. Phase inversion temperature is determined visually at the first sign of turbidity.

Suitable nonionic surfactants include: i) ethoxylated non-ionic surfactants prepared by the reaction of a monohydroxy alkanol or alkyphenol with 6 to 20 carbon atoms with preferably at least 12 moles particularly preferred at least 16 moles, and still more preferred at least 20 moles of ethylene oxide per mole of alcohol or alkylphenol; ii) alcohol alkoxylated surfactants having a from 6 to 20 carbon atoms and at least one ethoxy and propoxy group. Preferred for use herein are mixtures of surfactants i) and ii).

Another suitable non-ionic surfactants are epoxy-capped poly(oxyalkylated) alcohols represented by the formula:

$$R_1O[CH_2CH(CH_3)O]_x[CH_2CH_2O]_y[CH_2CH(OH)R_2] \quad (I)$$

wherein $R_1$ is a linear or branched, aliphatic hydrocarbon radical having from 4 to 18 carbon atoms; $R_2$ is a linear or branched aliphatic hydrocarbon radical having from 2 to 26 carbon atoms; x is an integer having an average value of from 0.5 to 1.5, more preferably about 1; and y is an integer having a value of at least 15, more preferably at least 20.

Preferably, the surfactant of formula I, at least about 10 carbon atoms in the terminal epoxide unit [CH$_2$CH(OH)R$_2$]. Suitable surfactants of formula I, according to the present invention, are Olin Corporation's POLY-TERGENT® SLF-18B nonionic surfactants, as described, for example, in WO 94/22800, published Oct. 13, 1994 by Olin Corporation.

Preferably non-ionic surfactants and/or system to use as anti-redeposition agents herein have a Draves wetting time of less than 360 seconds, preferably less than 200 seconds, more preferably less than 100 seconds and especially less than 60 seconds as measured by the Draves wetting method (standard method ISO 8022 using the following conditions; 3-g hook, 5-g cotton skein, 0.1% by weight aqueous solution at a temperature of 25° C.).

Amine oxides surfactants are also useful in the present invention as anti-redeposition surfactants include linear and branched compounds having the formula:

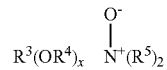

wherein $R^3$ is selected from an alkyl, hydroxyalkyl, acylamidopropyl and alkyl phenyl group, or mixtures thereof, containing from 8 to 26 carbon atoms, preferably 8 to 18 carbon atoms; $R^4$ is an alkylene or hydroxyalkylene group containing from 2 to 3 carbon atoms, preferably 2 carbon atoms, or mixtures thereof; x is from 0 to 5, preferably from 0 to 3; and each $R^5$ is an alkyl or hydroxyalkyl group containing from 1 to 3, preferably from 1 to 2 carbon atoms, or a polyethylene oxide group containing from 1 to 3, preferable 1, ethylene oxide groups. The $R^5$ groups can be attached to each other, e.g., through an oxygen or nitrogen atom, to form a ring structure.

These amine oxide surfactants in particular include $C_{10}$-$C_{18}$ alkyl dimethyl amine oxides and $C_8$-$C_{18}$ alkoxy ethyl dihydroxyethyl amine oxides. Examples of such materials include dimethyloctylamine oxide, diethyldecylamine oxide, bis-(2-hydroxyethyl)dodecylamine oxide, dimethyldodecylamine oxide, dipropyltetradecylamine oxide, methylethylhexadecylamine oxide, dodecylamidopropyl dimethylamine oxide, cetyl dimethylamine oxide, stearyl dimethylamine oxide, tallow dimethylamine oxide and dimethyl-2-hydroxyoctadecylamine oxide. Preferred are $C_{10}$-$C_{18}$ alkyl dimethylamine oxide, and $C_{10-18}$ acylamido alkyl dimethylamine oxide.

Anti-redeposition agents and in particular non-ionic surfactants may be present in amounts from 0 to 10% by weight, preferably from 0. 1% to 10%, and most preferably from 0.25% to 6%.

Sulfonated Polymer

The polymer, if used, is used in any suitable amount from about 0.1% to about 50%, preferably from 1% to about 20%, more preferably from 2% to 10% by weight of the composition. Sulfonated/carboxylated polymers are particularly suitable for the compositions contained in the pouch of the invention.

Suitable sulfonated/carboxylated polymers described herein may have a weight average molecular weight of less than or equal to about 100,000 Da, or less than or equal to about 75,000 Da, or less than or equal to about 50,000 Da, or from about 3,000 Da to about 50,000, preferably from about 5,000 Da to about 45,000 Da.

As noted herein, the sulfonated/carboxylated polymers may comprise (a) at least one structural unit derived from at least one carboxylic acid monomer having the general formula (I):

wherein $R^1$ to $R^4$ are independently hydrogen, methyl, carboxylic acid group or CH$_2$COOH and wherein the carboxylic acid groups can be neutralized; (b) optionally, one or more structural units derived from at least one nonionic monomer having the general formula (II):

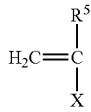

(II)

wherein $R^5$ is hydrogen, $C_1$ to $C_6$ alkyl, or $C_1$ to $C_6$ hydroxyalkyl, and X is either aromatic (with $R^5$ being hydrogen or methyl when X is aromatic) or X is of the general formula (III):

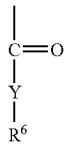

(III)

wherein $R^6$ is (independently of $R^5$) hydrogen, $C_1$ to $C_6$ alkyl, or $C_1$ to $C_6$ hydroxyalkyl, and Y is O or N; and at least one structural unit derived from at least one sulfonic acid monomer having the general formula (IV):

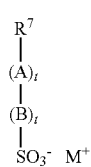

(IV)

wherein $R^7$ is a group comprising at least one $sp^2$ bond, A is O, N, P, S or an amido or ester linkage, B is a mono- or polycyclic aromatic group or an aliphatic group, each t is independently 0 or 1, and $M^+$ is a cation. In one aspect, $R^7$ is a $C_2$ to $C_6$ alkene. In another aspect, $R^7$ is ethene, butene or propene.

Preferred carboxylic acid monomers include one or more of the following: acrylic acid, maleic acid, itaconic acid, methacrylic acid, or ethoxylate esters of acrylic acids, acrylic and methacrylic acids being more preferred. Preferred sulfonated monomers include one or more of the following: sodium(meth)allyl sulfonate, vinyl sulfonate, sodium phenyl (meth)allyl ether sulfonate, or 2-acrylamido-methyl propane sulfonic acid. Preferred non-ionic monomers include one or more of the following: methyl(meth)acrylate, ethyl(meth)acrylate, t-butyl(meth)acrylate, methyl(meth)acrylamide, ethyl(meth)acrylamide, t-butyl(meth)acrylamide, styrene, or α-methyl styrene.

Preferably, the polymer comprises the following levels of monomers: from about 40 to about 90%, preferably from about 60 to about 90% by weight of the polymer of one or more carboxylic acid monomer; from about 5 to about 50%, preferably from about 10 to about 40% by weight of the polymer of one or more sulfonic acid monomer; and optionally from about 1% to about 30%, preferably from about 2 to about 20% by weight of the polymer of one or more non-ionic monomer. An especially preferred polymer comprises about 70% to about 80% by weight of the polymer of at least one carboxylic acid monomer and from about 20% to about 30% by weight of the polymer of at least one sulfonic acid monomer.

The carboxylic acid is preferably (meth)acrylic acid. The sulfonic acid monomer is preferably one of the following: 2-acrylamido methyl-1-propanesulfonic acid, 2-methacrylamido-2-methyl-1-propanesulfonic acid, 3-methacrylamido-2-hydroxypropanesulfonic acid, allysulfonic acid, methallysulfonic acid, allyloxybenzenesulfonic acid, methallyloxybenzensulfonic acid, 2-hydroxy-3-(2-propenyloxy)propanesulfonic acid, 2-methyl-2-propene-1-sulfonic acid, styrene sulfonic acid, vinylsulfonic acid, 3-sulfopropyl acrylate, 3-sulfopropyl methacrylate, sulfomethylacrylamid, sulfomethylmethacrylamide, and water soluble salts thereof. The unsaturated sulfonic acid monomer is most preferably 2-acrylamido-2-propanesulfonic acid (AMPS).

Preferred commercial available polymers include: Alcosperse 240, Aquatreat AR 540 and Aquatreat MPS supplied by Alco Chemical; Acumer 3100, Acumer 2000, Acusol 587G and Acusol 588G supplied by Rohm & Haas; Goodrich K-798, K-775 and K-797 supplied by BF Goodrich; and ACP 1042 supplied by ISP technologies Inc. Particularly preferred polymers are Acusol 587G and Acusol 588G supplied by Rohm & Haas.

In the polymers, all or some of the carboxylic or sulfonic acid groups can be present in neutralized form, i.e. the acidic hydrogen atom of the carboxylic and/or sulfonic acid group in some or all acid groups can be replaced with metal ions, preferably alkali metal ions and in particular with sodium ions.

Cleaning Actives

Any traditional cleaning ingredients can be used as part of the compositions of invention. The levels given are weight per cent and refer to the total composition (excluding the water-soluble film in the case of enveloped composition executions). The detergent compositions can be built or unbuilt and comprise one or more detergent active components which may be selected from bleach, bleach activator, bleach catalyst, surfactants, alkalinity sources, enzymes, polymeric dispersants, anti-corrosion agents (e.g. sodium silicate) and care agents. Highly preferred detergent components include a builder compound, an alkalinity source, an anti-redeposition agent, a sulfonated polymer, an enzyme and an additional bleaching agent.

Builder

Builders suitable for use herein include builder which forms water-soluble hardness ion complexes (sequestering builder) such as citrates and polyphosphates e.g. sodium tripolyphosphate and sodium tripolyphosphate hexahydrate, potassium tripolyphosphate and mixed sodium and potassium tripolyphosphate salts and builder which forms hardness precipitates (precipitating builder) such as carbonates e.g. sodium carbonate.

Other suitable builders include amino acid based compound or a succinate based compound. The term "succinate based compound" and "succinic acid based compound" are used interchangeably herein. Examples of suitable amino acid based compounds include MGDA (methyl-glycine-diacetic acid), and salts and derivatives thereof and GLDA (glutamic-N,N-diacetic acid) and salts and derivatives thereof. GLDA (salts and derivatives thereof) is especially preferred according to the invention, with the tetrasodium salt thereof being especially preferred. Other suitable builders are described in U.S. Pat. No. 6,426,229. Particular suitable builders include; for example, aspartic acid-N-monoacetic acid (ASMA), aspartic acid-N,N-diacetic acid (ASDA), aspartic acid-N-monopropionic acid (ASMP), iminodisuccinic acid (IDA), N-(2-sulfomethyl)aspartic acid (SMAS), N-(2-sulfoethyl)aspartic acid (SEAS), N-(2-sulfomethyl) glutamic acid (SMGL), N-(2-sulfoethyl)glutamic acid (SEGL), N-methyliminodiacetic acid (MIDA), α-alanine-N,N-diacetic acid (α-ALDA), serine-N,N-diacetic acid (SEDA), isoserine-N,N-diacetic acid (ISDA), phenylalanine- N,N-diacetic acid (PHDA), anthranilic acid-N,N-diacetic acid (ANDA), sulfanilic acid-N,N-diacetic acid (SLDA), taurine-N,N-diacetic acid (TUDA) and sulfomethyl-N,N-diacetic acid (SMDA) and alkali metal salts or ammonium salts thereof.

Preferably the amino acid based compound or succinate based compound is present in the composition in an amount of at least 1 wt %, preferably at least 5 wt %, more preferably at least 10 wt %, and most preferably at least 20 wt %. Preferably these compounds are present in an amount of up to 50 wt %, preferably up to 45 wt %, more preferably up to 40 wt %, and most preferably up to 35 wt %. It is preferred that the composition contains 20% wt or less of phosphorous-containing ingredients, more preferably 10% wt or less, most preferably that they are substantially free of such ingredients and even more preferably they are free of such ingredients.

Other builders include homopolymers and copolymers of polycarboxylic acids and their partially or completely neutralized salts, monomeric polycarboxylic acids and hydroxycarboxylic acids and their salts. Preferred salts of the above-mentioned compounds are the ammonium and/or alkali metal salts, i.e. the lithium, sodium, and potassium salts, and particularly preferred salts are the sodium salts.

Suitable polycarboxylic acids are acyclic, alicyclic, heterocyclic and aromatic carboxylic acids, in which case they contain at least two carboxyl groups which are in each case separated from one another by, preferably, no more than two carbon atoms. Polycarboxylates which comprise two carboxyl groups include, for example, water-soluble salts of, malonic acid, (ethyl enedioxy) diacetic acid, maleic acid, diglycolic acid, tartaric acid, tartronic acid and fumaric acid. Polycarboxylates which contain three carboxyl groups include, for example, water-soluble citrate. Correspondingly, a suitable hydroxycarboxylic acid is, for example, citric acid. Another suitable polycarboxylic acid is the homopolymer of acrylic acid. Other suitable builders are disclosed in WO 95/01416, to the contents of which express reference is hereby made.

The builder is typically present at a level of from about 30 to about 80%, preferably from about 40 to about 70% by weight of composition. It is also preferred that the ratio of sequestering builder to precipitating builder is from about 10:1 to about 1:1, preferably from about 8:1 to 2:1.

Silicates

Preferred silicates are sodium silicates such as sodium disilicate, sodium metasilicate and crystalline phyllosilicates. Silicates if present are at a level of from about 1 to about 20%, preferably from about 5 to about 15% by weight of composition.

Bleach

Inorganic and organic bleaches are suitable cleaning actives for use herein. Inorganic bleaches include perhydrate salts such as perborate, percarbonate, perphosphate, persulfate and persilicate salts. The inorganic perhydrate salts are normally the alkali metal salts. The inorganic perhydrate salt may be included as the crystalline solid without additional protection. Alternatively, the salt can be coated.

Alkali metal percarbonates, particularly sodium percarbonate are preferred perhydrates for use herein. The percarbonate is most preferably incorporated into the products in a coated form which provides in-product stability. A suitable coating material providing in product stability comprises mixed salt of a water-soluble alkali metal sulphate and carbonate. Such coatings together with coating processes have previously been described in GB-1,466,799. The weight ratio of the mixed salt coating material to percarbonate lies in the range from 1:200 to 1:4, more preferably from 1:99 to 19, and most preferably from 1:49 to 1:19. Preferably, the mixed salt is of sodium sulphate and sodium carbonate which has the general formula $Na_2SO_4 \cdot n \cdot Na_2CO_3$ wherein n is from 0.1 to 3, preferably n is from 0.3 to 1.0 and most preferably n is from 0.2 to 0.5.

Another suitable coating material providing in product stability, comprises sodium silicate of $SiO_2:Na_2O$ ratio from 1.8:1 to 3.0:1, preferably L8:1 to 2.4:1, and/or sodium metasilicate, preferably applied at a level of from 2% to 10%, (normally from 3% to 5%) Of $SiO_2$ by weight of the inorganic perhydrate salt. Magnesium silicate can also be included in the coating. Coatings that contain silicate and borate salts or boric acids or other inorganics are also suitable.

Other coatings which contain waxes, oils, fatty soaps can also be used advantageously within the present invention.

Potassium peroxymonopersulfate is another inorganic perhydrate salt of utility herein.

Typical organic bleaches are organic peroxyacids including diacyl and tetraacylperoxides, especially diperoxydodecanedioc acid, diperoxytetradecanedioc acid, and diperoxyhexadecanedioc acid. Dibenzoyl peroxide is a preferred organic peroxyacid herein. Mono- and diperazelaic acid, mono- and diperbrassylic acid, and Nphthaloylaminoperoxicaproic acid are also suitable herein.

The diacyl peroxide, especially dibenzoyl peroxide, should preferably be present in the form of particles having a weight average diameter of from about 0.1 to about 100 microns, preferably from about 0.5 to about 30 microns, more preferably from about 1 to about 10 microns. Preferably, at least about 25%, more preferably at least about 50%, even more preferably at least about 75%, most preferably at least about 90%, of the particles are smaller than 10 microns, preferably smaller than 6 microns. Diacyl peroxides within the above particle size range have also been found to provide better stain removal especially from plastic dishware, while minimizing undesirable deposition and filming during use in automatic dishwashing machines, than larger diacyl peroxide particles. The preferred diacyl peroxide particle size thus allows the formulator to obtain good stain removal with a low level of diacyl peroxide, which reduces deposition and filming. Conversely, as diacyl peroxide particle size increases, more diacyl peroxide is needed for good stain removal, which increases deposition on surfaces encountered during the dishwashing process.

Further typical organic bleaches include the peroxy acids, particular examples being the alkylperoxy acids and the arylperoxy acids. Preferred representatives are (a) peroxybenzoic acid and its ring-substituted derivatives, such as alkylperoxybenzoic acids, but also peroxy-α-naphthoic acid and magnesium monoperphthalate, (b) the aliphatic or substituted aliphatic peroxy acids, such as peroxylauric acid, peroxystearic acid, ε-phthalimidoperoxycaproic acid[phthaloiminoperoxyhexanoic acid (PAP)], o-carboxybenzamidoperoxycaproic acid, N-nonenylamidoperadipic acid and N-nonenylamidopersuccinates, and (c) aliphatic and araliphatic peroxydicarboxylic acids, such as 1,12-diperoxycarboxylic acid, 1,9-diperoxyazelaic acid, diperoxysebacic acid, diperoxybrassylic acid, the diperoxyphthalic acids, 2-decyldiperoxybutane-1,4-dioic acid, N,N-terephthaloyldi (6-aminopercaproic acid).

Bleach Activators

Bleach activators are typically organic peracid precursors that enhance the bleaching action in the course of cleaning at temperatures of 60° C. and below. Bleach activators suitable for use herein include compounds which, under perhydrolysis conditions, give aliphatic peroxoycarboxylic acids having preferably from 1 to 10 carbon atoms, in particular from 2 to 4 carbon atoms, and/or optionally substituted perbenzoic acid. Suitable substances bear O-acyl and/or N-acyl groups of the number of carbon atoms specified and/or optionally substituted benzoyl groups. Preference is given to polyacylated alkylenediamines, in particular tetraacetylethylenediamine (TAED), acylated triazine derivatives, in particular 1,5-diacetyl-2,4-dioxohexahydro-1,3,5-triazine (DADHT), acylated glycolurils, in particular tetraacetylglycoluril (TAGU), N-acylimides, in particular N-nonanoylsuccinimide (NOSI), acylated phenolsulfonates, in particular n-nonanoyl- or isononanoyloxybenzenesulfonate (n- or iso-NOBS), carboxylic anhydrides, in particular phthalic anhydride, acylated polyhydric alcohols, in particular triacetin, ethylene glycol diacetate and 2,5-diacetoxy-2,5-dihydrofuran and also triethylacetyl citrate (TEAC). Bleach activators if included in the compositions of the invention are in a level of from about 0.1 to about 10%, preferably from about 0.5 to about 2% by weight of the composition.

Bleach Catalyst

Bleach catalysts preferred for use herein include the manganese triazacyclononane and related complexes (U.S. Pat. Nos. 4,246,612, 5,227,084); Co, Cu, Mn and Fe bispyridylamine and related complexes (U.S. Pat. No. 5,114,611); and pentamine acetate cobalt(III) and related complexes (U.S. Pat. No. 4,810,410). A complete description of bleach catalysts suitable for use herein can be found in WO 99/06521, pages 34, line 26 to page 40, line 16. Bleach catalyst if included in the compositions of the invention are in a level of from about 0.1 to about 10%, preferably from about 0.5 to about 2% by weight of the composition.

Metal Care Agents

Metal care agents may prevent or reduce the tarnishing, corrosion or oxidation of metals, including aluminium, stainless steel and non-ferrous metals, such as silver and copper. Suitable examples include one or more of the following:
(a) benzatriazoles, including benzotriazole or bis-benzotriazole and substituted derivatives thereof. Benzotriazole derivatives are those compounds in which the available substitution sites on the aromatic ring are partially or completely substituted. Suitable substituents include linear or branch-chain $C_1$-$C_{20}$-alkyl groups and hydroxyl, thio, phenyl or halogen such as fluorine, chlorine, bromine and iodine.
(b) metal salts and complexes chosen from the group consisting of zinc, manganese, titanium, zirconium, hafnium, vanadium, cobalt, gallium and cerium salts and/or complexes, the metals being in one of the oxidation states II, III, IV, V or VI. In one aspect, suitable metal salts and/or metal complexes may be chosen from the group consisting of Mn(II) sulphate, Mn(II) citrate, Mn(II) stearate, Mn(II) acetylacetonate, $K_2TiF_6$, $K_2ZrF_6$, $CoSO_4$, $Co(NO_3)_2$ and $Ce(NO_3)_3$, zinc salts, for example zinc sulphate, hydrozincite or zinc acetate;
(c) silicates, including sodium or potassium silicate, sodium disilicate, sodium metasilicate, crystalline phyllosilicate and mixtures thereof.

Further suitable organic and inorganic redox-active substances that act as silver/copper corrosion inhibitors are disclosed in WO 94/26860 and WO 94/26859.

Preferably the composition of the invention comprises from 0.1 to 5% by weight of the composition of a metal care agent, preferably the metal care agent is a zinc salt.

Unit Dose

Products in unit dose form include tablets, capsules, sachets, pouches, etc. Preferred for use herein are pouches, in particular multi-compartment pouches.

A multi-compartment pouch is formed by a plurality of water-soluble films which form a plurality of compartments. The pouch preferably comprises at least two side-by-side compartments superposed (i.e., placed above) onto another compartment. This disposition contributes to the compactness, robustness and strength of the pouch, additionally, it minimise the amount of water-soluble film required. It only requires three pieces of film to form three compartments. The robustness of the pouch allows also for the use of very thin films without compromising the physical integrity of the pouch. The pouch is also very easy to use because the compartments do not need to be folded to be used in dispensers of fix geometry. At least two of the compartments of the pouch contain two different compositions. By "different compositions" herein is meant compositions that differ in at least one ingredient.

Preferably, at least one of the compartments contains a solid composition and another compartment a liquid composition, the compositions are preferably in a solid to liquid weight ratio of from about 20:1 to about 1:20, more preferably from about 18:1 to about 2:1 and even more preferably from about 15:1 to about 5:1. The pouch of the invention is very versatile because it can accommodate compositions having a broad spectrum of values of solid:liquid ratio. Particularly preferred have been found to be pouches having a high solid:liquid ratio because many of the detergent ingredients are most suitable for use in solid form, preferably in powder form. The ratio solid:liquid defined herein refers to the relationship between the weight of all the solid compositions and the weight of all the liquid compositions in the pouch.

In other embodiments the solid:liquid weight ratio is from about 2:1 to about 18:1, more preferably from about 5:1 to about 15:1. These weight ratios are suitable in cases in which most of the ingredients of the detergent are in liquid form.

In preferred embodiments the two side-by-side compartments contain liquid compositions, which can be the same but preferably are different and another compartment contains a solid composition, preferably in powder form, more preferably a densified powder. The solid composition contributes to the strength and robustness of the pouch. The liquid compositions contribute to the stability of the pouch, in particular if the solid composition comprises moisture sensitive ingredients (such as bleach). This is more so if the compartments superposed onto the solid-containing compartment cover completely the top surface (i.e. the common solid/liquid surface) of the solid-containing compartment.

For dispenser fit reasons the unit dose form products herein have a square or rectangular base and a height of from about 1 to about 5 cm, more preferably from about 1 to about 4 cm. Preferably the weight of the solid composition is from about 10 to about 22 grams, more preferably from about 15 to about 20 grams and the weight of the liquid compositions is from about 0.5 to about 4 grams, more preferably from about 0.8 to about 3 grams.

The multi-compartment pouch of the invention is very versatile in terms of dissolution profile. In preferred embodiments, at least two of the films which form different compartments have different solubility, under the same conditions, releasing the content of the compositions which they partially or totally envelope at different times. The term "solubility" as used herein is not intended to refer to total solubility of a film but to the point at which the pouch in the wash solution breaks to release its content.

Enzymes, and in particular amylases, can lose stability in product, due to its interaction with bleach and builders (they can destabilize the enzyme by binding to the calcium of the enzymes). In addition, the performance of enzymes in a cleaning solution can be impaired by the alkalinity of the solution, bleach, builders, etc. In preferred embodiments, one of the compositions of the multi-compartment pouch, preferably a solid composition, comprises bleach and another composition, preferably a composition in liquid form, comprises enzymes. It is also preferred that one of the films enclosing the enzyme-comprising composition dissolves prior to the films enclosing the bleach-containing composition during the main-wash cycle of an automatic dishwashing machine, thereby releasing the enzyme-containing composition into the wash liquor prior to the delivery of the bleach-containing composition. This gives the enzymes the possibility to operate under optimum condition, avoiding interactions with other detergent actives. The pouch provides excellent cleaning. It is preferred that the bleach-containing composition comprises also a builder.

Controlled release of the ingredients of a multi-compartment pouch can be achieved by modifying the thickness of the film and/or the solubility of the film material. The solubility of the film material can be delayed by for example cross-linking the film as described in WO 02/102,955 at pages 17 and 18. Other water-soluble films designed for rinse release are described in U.S. Pat. Nos. 4,765,916 and 4,972,017. Waxy coating (see WO 95/29982) of films can help with rinse release. pH controlled release means are described in WO 04/111178, in particular amino-acetylated polysaccharide having selective degree of acetylation.

Other means of obtaining delayed release by multi-compartment pouches with different compartments, where the compartments are made of films having different solubility are taught in WO 02/08380.

Abbreviations Used in the Example

In the example, the abbreviated component identifications have the following meanings:

| | |
|---|---|
| Carbonate | Anhydrous sodium carbonate |
| STPP | Sodium tripolyphosphate anhydrous |
| Silicate | Amorphous Sodium Silicate ($SiO_2$:$Na_2O$ = from 2:1 to 4:1) |
| Alcosperse 240-D | Sulfonated polymer available from Alco Chemical 95% solids |
| Percarbonate | Sodium percarbonate of the nominal formula $2Na_2CO_3 \cdot 3H_2O_2$ |
| TAED | Tetraacetylethylenediamine |
| Detergency enzyme | available from Novozymes A/S |
| SLF18 | Non-ionic surfactant available from BASF |
| Neodol 1-9 | Non-ionic surfactant available from Shell |
| DPG | dipropylene glycol |

In the following example all levels are quoted in per cent by weight of the composition (either solid or liquid composition).

EXAMPLE

The compositions tabulated below are introduced into a multi-compartment pouch having a first compartment comprising the solid composition (in powder form) and a liquid compartment superposed onto the powder compartment comprising the liquid compositions. The film used is Monosol M8630 film as supplied by Monosol. The weight of the solid composition is 17 grams and the weight of liquid compositions is 2.6 gram.

The pouch also comprises 0.3 mg of active low temperature amylase and 2 mg of active variant protease per gram of composition.

| Ingredient | Level (% wt) |
|---|---|
| Solid composition | |
| STPP | 35 |
| Carbonate | 24 |
| Silicate | 7 |
| TAED | 0.5 |
| Zinc carbonate | 0.5 |
| SLF18 | 1.5 |
| Percarbonate | 15 |
| Alcosperse 240D | 10 |
| Processing aids | To balance |
| Liquid composition | |
| DPG | 45 |
| SLF18 | 45 |
| Neodol 1-9 | 3 |
| Glycerine | 2 |
| Processing aids | To balance |

The exemplified pouch is used to wash a soiled load as described herein below in an automatic dishwasher under the conditions described herein below. The washing items present excellent shine.

Substrates/Soils
  Corning ware round casserole dish with egg.
    1 part of butter with 50 cc of egg in microwave 4½ minutes.
    2 casserole dishes per run
  Stainless steel pot
    Painted with 10 grams of cooked and blended Kraft Macaroni and cheese
    Baked in over for seven minutes
    2 stainless steel pots per run
  China Vertex plate
    Painted with five grams of cooked and blended Minute Rice
    Dry overnight
    2 plates per run
  Black Ceramic Plates
    Painted with 5 grams of a composite soil (TMD) comprising eggs, vegetables, meat, and cereals.
    Allowed to dry over night
    4 plates per run
    TMD soil is made by J&R.
  Stainless Steel Spatulas
    Painted with five grams of TMD soil
    Allowed to dry overnight
    4 spatulas per run Test Conditions:
  Bank of four machines GE2600
  City Water (8 gpg)
  Four products
  120° F. Inlet Water temperature
  Normal cycle/heated dry
  Substrates listed above are placed in the dishwasher
  50 grams of the TMD soil is added when the main wash cup opens The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An automatic dishwashing detergent composition comprising:
   a. at least 0.1 mg of active protease per gram of composition, wherein the protease is a variant of a protease that has at least 70% identity with the amino acid sequence of SEQ ID NO:1. wherein said variant comprise variations in one or more of the following positions: 32, 33, 48-54, 58-62, 94-107, 116, 123-133, 150, 152-156, 158-161, 164, 169, 175-186, 197, 198, 203-216 as compared with the protease in SEQ ID NO:1; and
   b. at least 0.05 mg of an active low temperature amylase per gram of composition, wherein the low temperature amylase is a variant with:
      a. one or more substitutions in the following positions versus SEQ ID NO: 2: 9, 26, 149, 182, 186, 202, 257, 295, 299, 323, 339 and 345; and, optionally, with one or more of the substitutions and/or deletions in the following positions: 118, 183, 184, 195, 320 and 458, which if present, comprise R118K, D183*, G184*, N195F, R320K and/or R458K; or
      b. at least one substitution in the following positions versus SEQ ID NO:4: M202, M208, S255, R172, and/or M261.

2. An automatic dishwashing detergent composition according to claim 1 wherein the protease comprises the variations G116V+S126L+P127Q+S128A.

3. An automatic dishwashing detergent composition according to claim 1 comprising at least 1.5 mg of active protease per gram of the composition.

4. An automatic dishwashing detergent composition according to claim 3 further comprising at least about 0.2 mg of low temperature amylase per gram of composition.

5. An automatic dishwashing detergent composition according to claim 1 further comprising a lipase.

6. An automatic dishwashing detergent composition according to claim 1 further comprising an anti-redeposition agent and/or a sulfonated polymer.

7. An automatic dishwashing detergent composition according to claim 1 wherein the composition is in the form of a water-soluble pouch and wherein the weight of the composition is from about 10 to about 25 grams.

8. The automatic dishwashing detergent composition according to claim 7, wherein the pouch is a multi-compartment pouch having a plurality of films forming a plurality of compartments.

9. The automatic dishwashing detergent composition according to claim 8, wherein the pouch comprises two side-by-side compartments superposed onto another compartment and at least two different compartments, respectively comprising two different compositions.

10. A method of dishwashing in an automatic dishwashing machine using a detergent composition according to claim 1 wherein the composition is in unit dose form and the weight of the composition is from about 10 to about 25 grams comprising the steps of placing the pouch into the product dispenser and releasing it during the main-wash cycle.

* * * * *

(12) EX PARTE REEXAMINATION CERTIFICATE (10419th)
United States Patent
Souter

(10) Number: US 8,008,241 C1
(45) Certificate Issued: Nov. 26, 2014

(54) AUTOMATIC DISHWASHING DETERGENT COMPOSITION

(75) Inventor: Philip Frank Souter, Morpeth (GB)

(73) Assignee: The Procter & Gamble Company, Cincinnati, OH (US)

Reexamination Request:
No. 90/012,512, Sep. 12, 2012

Reexamination Certificate for:
Patent No.: 8,008,241
Issued: Aug. 30, 2011
Appl. No.: 12/397,489
Filed: Mar. 4, 2009

(30) Foreign Application Priority Data

Mar. 14, 2008 (EP) ..................... 08152749
Sep. 16, 2008 (EP) ..................... 08164650

(51) Int. Cl.
| | |
|---|---|
| *C11D 3/386* | (2006.01) |
| *C12N 9/54* | (2006.01) |
| *C12N 9/28* | (2006.01) |
| *C11D 3/37* | (2006.01) |
| *C11D 17/04* | (2006.01) |

(52) U.S. Cl.
CPC ............ *C11D 3/378* (2013.01); *C11D 3/38609* (2013.01); *C11D 3/38618* (2013.01); *C11D 3/38627* (2013.01); *C11D 17/042* (2013.01)
USPC ............................ 510/226; 435/202; 435/221

(58) Field of Classification Search
None
See application file for complete search history.

(56) References Cited

To view the complete listing of prior art documents cited during the proceeding for Reexamination Control Number 90/012,512, please refer to the USPTO's public Patent Application Information Retrieval (PAIR) system under the Display References tab.

*Primary Examiner* — Sharon Turner

(57) ABSTRACT

An automatic dishwashing detergent composition comprising:
a. at least 0.1 mg of active protease per gram of composition, wherein the protease is a variant of a protease that has at least 70% identity with the amino acid sequence of SEQ ID NO:1. wherein said variant comprise variations in one or more of the following positions: 32, 33, 48-54, 58-62, 94-107, 116, 123-133, 150, 152-156, 158-161, 164, 169, 175-186, 197, 198, 203-216 as compared with the protease in SEQ ID NO:1; and
b. at least 0.05 mg of an active low temperature amylase per gram of composition.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1-10 is confirmed.

New claim 11 is added and determined to be patentable.

*11. An automatic dishwashing detergent composition according to claim 1 comprising a sulfonated polymer.*

\* \* \* \* \*

SEQUENCE LISTING

<160> NUMBER OF SEQ ID NOS: 4

<210> SEQ ID NO 1
<211> LENGTH: 269
<212> TYPE: PRT
<213> ORGANISM: Bacillus Alkalophilus PB92

<400> SEQUENCE: 1

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Asn Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265

<210> SEQ ID NO 2
<211> LENGTH: 485
<212> TYPE: PRT
<213> ORGANISM: Bacillus AA560

<400> SEQUENCE: 2

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
            20                  25                  30

Asn Leu Lys Asp Lys Gly Ile Ser Ala Val Trp Ile Pro Pro Ala Trp
        35                  40                  45

-continued

```
Lys Gly Ala Ser Gln Asn Asp Val Gly Tyr Gly Ala Tyr Asp Leu Tyr
 50                  55                  60

Asp Leu Gly Glu Phe Asn Gln Lys Gly Thr Ile Arg Thr Lys Tyr Gly
 65                  70                  75                  80

Thr Arg Asn Gln Leu Gln Ala Ala Val Asn Ala Leu Lys Ser Asn Gly
                 85                  90                  95

Ile Gln Val Tyr Gly Asp Val Val Met Asn His Lys Gly Gly Ala Asp
                100                 105                 110

Ala Thr Glu Met Val Arg Ala Val Glu Val Asn Pro Asn Asn Arg Asn
                115                 120                 125

Gln Glu Val Ser Gly Glu Tyr Thr Ile Glu Ala Trp Thr Lys Phe Asp
130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Lys Leu Asn Asn Arg
                165                 170                 175

Ile Tyr Lys Phe Arg Gly Asp Gly Lys Gly Trp Asp Trp Glu Val Asp
                180                 185                 190

Thr Glu Asn Gly Asn Tyr Asp Tyr Leu Met Tyr Ala Asp Ile Asp Met
                195                 200                 205

Asp His Pro Glu Val Val Asn Glu Leu Arg Asn Trp Gly Val Trp Tyr
210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
                245                 250                 255

Thr Gly Lys Asn Met Phe Ala Val Ala Glu Phe Trp Lys Asn Asp Leu
                260                 265                 270

Gly Ala Ile Glu Asn Tyr Leu Asn Lys Thr Asn Trp Asn His Ser Val
                275                 280                 285

Phe Asp Val Pro Leu His Tyr Asn Leu Tyr Asn Ala Ser Lys Ser Gly
290                 295                 300

Gly Asn Tyr Asp Met Arg Gln Ile Phe Asn Gly Thr Val Val Gln Arg
305                 310                 315                 320

His Pro Met His Ala Val Thr Phe Val Asp Asn His Asp Ser Gln Pro
                325                 330                 335

Glu Glu Ala Leu Glu Ser Phe Val Glu Glu Trp Phe Lys Pro Leu Ala
                340                 345                 350

Tyr Ala Leu Thr Leu Thr Arg Glu Gln Gly Tyr Pro Ser Val Phe Tyr
                355                 360                 365

Gly Asp Tyr Tyr Gly Ile Pro Thr His Gly Val Pro Ala Met Lys Ser
370                 375                 380

Lys Ile Asp Pro Ile Leu Glu Ala Arg Gln Lys Tyr Ala Tyr Gly Arg
385                 390                 395                 400

Gln Asn Asp Tyr Leu Asp His His Asn Ile Ile Gly Trp Thr Arg Glu
                405                 410                 415

Gly Asn Thr Ala His Pro Asn Ser Gly Leu Ala Thr Ile Met Ser Asp
                420                 425                 430

Gly Ala Gly Gly Asn Lys Trp Met Phe Val Gly Arg Asn Lys Ala Gly
                435                 440                 445

Gln Val Trp Thr Asp Ile Thr Gly Asn Arg Ala Gly Thr Val Thr Ile
                450                 455                 460

Asn Ala Asp Gly Trp Gly Asn Phe Ser Val Asn Gly Gly Ser Val Ser
465                 470                 475                 480
```

```
Ile Trp Val Asn Lys
              485

<210> SEQ ID NO 3
<211> LENGTH: 483
<212> TYPE: PRT
<213> ORGANISM: Bacillus Licheniformis

<400> SEQUENCE: 3

Ala Asn Leu Asn Gly Thr Leu Met Gln Tyr Phe Glu Trp Tyr Met Pro
1               5                   10                  15

Asn Asp Gly Gln His Trp Arg Arg Leu Gln Asn Asp Ser Ala Tyr Leu
            20                  25                  30

Ala Glu His Gly Ile Thr Ala Val Trp Ile Pro Pro Ala Tyr Lys Gly
        35                  40                  45

Thr Ser Gln Ala Asp Val Gly Tyr Gly Ala Tyr Asp Leu Tyr Asp Leu
    50                  55                  60

Gly Glu Phe His Gln Lys Gly Thr Val Arg Thr Lys Tyr Gly Thr Lys
65                  70                  75                  80

Gly Glu Leu Gln Ser Ala Ile Lys Ser Leu His Ser Arg Asp Ile Asn
                85                  90                  95

Val Tyr Gly Asp Val Val Ile Asn His Lys Gly Gly Ala Asp Ala Thr
            100                 105                 110

Glu Asp Val Thr Ala Val Glu Val Asp Pro Ala Asp Arg Asn Arg Val
        115                 120                 125

Ile Ser Gly Glu His Arg Ile Lys Ala Trp Thr His Phe His Phe Pro
    130                 135                 140

Gly Arg Gly Ser Thr Tyr Ser Asp Phe Lys Trp His Trp Tyr His Phe
145                 150                 155                 160

Asp Gly Thr Asp Trp Asp Glu Ser Arg Lys Leu Asn Arg Ile Tyr Lys
                165                 170                 175

Phe Gln Gly Lys Ala Trp Asp Trp Glu Val Ser Asn Glu Asn Gly Asn
            180                 185                 190

Tyr Asp Tyr Leu Met Tyr Ala Asp Ile Asp Tyr Asp His Pro Asp Val
        195                 200                 205

Ala Ala Glu Ile Lys Arg Trp Gly Thr Trp Tyr Ala Asn Glu Leu Gln
    210                 215                 220

Leu Asp Gly Phe Arg Leu Asp Ala Val Lys His Ile Lys Phe Ser Phe
225                 230                 235                 240

Leu Arg Asp Trp Val Asn His Val Arg Glu Lys Thr Gly Lys Glu Met
                245                 250                 255

Phe Thr Val Ala Glu Tyr Trp Gln Asn Asp Leu Gly Ala Leu Glu Asn
            260                 265                 270

Tyr Leu Asn Lys Thr Asn Phe Asn His Ser Val Phe Asp Val Pro Leu
        275                 280                 285

His Tyr Gln Phe His Ala Ala Ser Thr Gln Gly Gly Gly Tyr Asp Met
    290                 295                 300

Arg Lys Leu Leu Asn Ser Thr Val Val Ser Lys His Pro Leu Lys Ala
305                 310                 315                 320

Val Thr Phe Val Asp Asn His Asp Thr Gln Pro Gly Gln Ser Leu Glu
                325                 330                 335

Ser Thr Val Gln Thr Trp Phe Lys Pro Leu Ala Tyr Ala Phe Ile Leu
            340                 345                 350

Thr Arg Glu Ser Gly Tyr Pro Gln Val Phe Tyr Gly Asp Met Tyr Gly
        355                 360                 365
```

```
Thr Lys Gly Asp Ser Gln Arg Glu Ile Pro Ala Leu Lys His Lys Ile
    370                 375                 380

Glu Pro Ile Leu Lys Ala Arg Lys Gln Tyr Ala Tyr Gly Ala Gln His
385                 390                 395                 400

Asp Tyr Phe Asp His His Asp Ile Val Gly Trp Thr Arg Glu Gly Asp
                405                 410                 415

Ser Ser Val Ala Asn Ser Gly Leu Ala Ala Leu Ile Thr Asp Gly Pro
            420                 425                 430

Gly Gly Ala Lys Arg Met Tyr Val Gly Arg Gln Asn Ala Gly Glu Thr
        435                 440                 445

Trp His Asp Ile Thr Gly Asn Arg Ser Glu Pro Val Val Ile Asn Ser
    450                 455                 460

Glu Gly Trp Gly Glu Phe His Val Asn Gly Gly Ser Val Ser Ile Tyr
465                 470                 475                 480

Val Gln Arg

<210> SEQ ID NO 4
<211> LENGTH: 485
<212> TYPE: PRT
<213> ORGANISM: Bacillus sp. 707

<400> SEQUENCE: 4

His His Asn Gly Thr Asn Gly Thr Met Met Gln Tyr Phe Glu Trp Tyr
1               5                   10                  15

Leu Pro Asn Asp Gly Asn His Trp Asn Arg Leu Asn Ser Asp Ala Ser
            20                  25                  30

Asn Leu Lys Ser Lys Gly Ile Thr Ala Val Trp Ile Pro Pro Ala Trp
        35                  40                  45

Lys Gly Ala Ser Gln Asn Asp Val Gly Tyr Gly Ala Tyr Asp Leu Tyr
50                  55                  60

Asp Leu Gly Glu Phe Asn Gln Lys Gly Thr Val Arg Thr Lys Tyr Gly
65                  70                  75                  80

Thr Arg Ser Gln Leu Gln Ala Ala Val Thr Ser Leu Lys Asn Asn Gly
                85                  90                  95

Ile Gln Val Tyr Gly Asp Val Val Met Asn His Lys Gly Gly Ala Asp
            100                 105                 110

Ala Thr Glu Met Val Arg Ala Val Glu Val Asn Pro Asn Asn Arg Asn
        115                 120                 125

Gln Glu Val Thr Gly Glu Tyr Thr Ile Glu Ala Trp Thr Arg Phe Asp
130                 135                 140

Phe Pro Gly Arg Gly Asn Thr His Ser Ser Phe Lys Trp Arg Trp Tyr
145                 150                 155                 160

His Phe Asp Gly Val Asp Trp Asp Gln Ser Arg Arg Leu Asn Asn Arg
                165                 170                 175

Ile Tyr Lys Phe Arg Gly His Gly Lys Ala Trp Asp Trp Glu Val Asp
            180                 185                 190

Thr Glu Asn Gly Asn Tyr Asp Tyr Leu Met Tyr Ala Asp Ile Asp Met
        195                 200                 205

Asp His Pro Glu Val Val Asn Glu Leu Arg Asn Trp Gly Val Trp Tyr
210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
                245                 250                 255
```

-continued

```
Thr Gly Lys Asn Met Phe Ala Val Ala Glu Phe Trp Lys Asn Asp Leu
        260                 265                 270

Gly Ala Ile Glu Asn Tyr Leu Gln Lys Thr Asn Trp Asn His Ser Val
        275                 280                 285

Phe Asp Val Pro Leu His Tyr Asn Leu Tyr Asn Ala Ser Lys Ser Gly
        290                 295                 300

Gly Asn Tyr Asp Met Arg Asn Ile Phe Asn Gly Thr Val Val Gln Arg
305                 310                 315                 320

His Pro Ser His Ala Val Thr Phe Val Asp Asn His Asp Ser Gln Pro
                325                 330                 335

Glu Glu Ala Leu Glu Ser Phe Val Glu Glu Trp Phe Lys Pro Leu Ala
            340                 345                 350

Tyr Ala Leu Thr Leu Thr Arg Glu Gln Gly Tyr Pro Ser Val Phe Tyr
            355                 360                 365

Gly Asp Tyr Tyr Gly Ile Pro Thr His Gly Val Pro Ala Met Arg Ser
        370                 375                 380

Lys Ile Asp Pro Ile Leu Glu Ala Arg Gln Lys Tyr Ala Tyr Gly Lys
385                 390                 395                 400

Gln Asn Asp Tyr Leu Asp His His Asn Ile Ile Gly Trp Thr Arg Glu
                405                 410                 415

Gly Asn Thr Ala His Pro Asn Ser Gly Leu Ala Thr Ile Met Ser Asp
            420                 425                 430

Gly Ala Gly Gly Ser Lys Trp Met Phe Val Gly Arg Asn Lys Ala Gly
        435                 440                 445

Gln Val Trp Ser Asp Ile Thr Gly Asn Arg Thr Gly Thr Val Thr Ile
    450                 455                 460

Asn Ala Asp Gly Trp Gly Asn Phe Ser Val Asn Gly Gly Ser Val Ser
465                 470                 475                 480

Ile Trp Val Asn Lys
                485
```